United States Patent [19]

Ramachandran et al.

[11] Patent Number: 5,008,412
[45] Date of Patent: Apr. 16, 1991

[54] PROCESS FOR THE PRODUCTION OF OXIDES

[75] Inventors: Ramakrishnan Ramachandran; Donald L. MacLean, both of Annandale; Donald P. Satchell, Jr., Summit, all of N.J.

[73] Assignee: The BOC Group, Inc., New Providence, N.J.

[21] Appl. No.: 376,331

[22] Filed: Jul. 6, 1989

Related U.S. Application Data

[63] Continuation-in-part of Ser. No. 215,859, Jul. 6, 1988, Pat. No. 4,859,537, which is a continuation-in-part of Ser. No. 154,157, Feb. 9, 1988, abandoned.

[51] Int. Cl.$^5$ ............... C07D 301/04; C07D 301/08; C07D 301/10
[52] U.S. Cl. .................... 549/523; 549/534; 549/535; 549/536; 568/411; 568/475; 585/654; 585/659
[58] Field of Search ............... 549/523, 534, 535, 536

[56] References Cited

U.S. PATENT DOCUMENTS

| | | | |
|---|---|---|---|
| 3,176,444 | 4/1965 | Kiyonaga | 55/26 |
| 4,498,910 | 2/1985 | Benkmann | 55/18 |
| 4,609,502 | 9/1986 | Khoobiar et al. | 558/319 X |
| 4,754,059 | 6/1988 | Khoobiar et al. | 558/320 |
| 4,849,538 | 7/1989 | Ramachandran et al. | 558/319 |
| 4,868,330 | 9/1989 | Ramachandran et al. | 558/319 X |
| 4,870,201 | 9/1989 | Ramachandran et al. | 558/319 |

OTHER PUBLICATIONS

Solomons, "Organic Chemistry", p. 212, 2nd ed. (1978), John Wiley & Sons.

*Primary Examiner*—Joseph Paul Brust
*Attorney, Agent, or Firm*—Carol A. Nemetz; Robert I. Pearlman

[57] ABSTRACT

An improved process is provided for the production of oxides from alkanes by reaction with oxygen, air or a gas enriched in oxygen relative to an air in the presence of an oxidation catalyst. An alkane, e.g. propane, is converted to an alkene in a multistage dehydrogenator. The product stream is withdrawn from an intermediate reactor in the dehydrogenator, other than the first and the last reactor, and introduced into an oxidation reactor. The product formed in the oxidation reactor is recovered in a conventional quench tower. The gaseous effluent from the quench tower is treated in a pressure swing adsorption (PSA) unit to form a gaseous stream containing the unreacted alkane and alkene as well as a minor amount, i.e. less than about 2 percent by volume, of oxygen and nitrogen, if present in the feed to the oxidation reactor. The gaseous stream, which may or may not contain hydrogen depending on the adsorbent in the PSA unit, is introduced into the reactor in the dehydrogenator following the intermediate reactor. The effluent from the last reactor in the dehydrogenator is introduced into either: (i) the first reactor; (ii) a reactor other than said first reactor wherein the alkene concentration closely approximates the effluent of the oxidation reactor. The subject process is particularly efficient utilizing oxygen-enriched air in the reactor feed. A preferred PSA system for use in the subject process comprises two parallel PSA units containing different adsorbents such that the gaseous phase formed in one contains all of the hydrogen in the gas phase from the quench tower. The feed to the PSA units is divided disproportionately so that the combined PSA effluent recycle streams contain the optimum concentration of hydrogen for the dehydrogenator.

22 Claims, 5 Drawing Sheets

PROCESS FOR THE PRODUCTION OF OXIDES

RELATED APPLICATIONS

This application is a continuation in part of U.S. patent application Ser. No. 07/215,859, filed July 6, 1988, now U.S. Pat. No. 4,849,537 which is a continuation-in-part of U.S. patent application Ser. No. 07/154,157, filed Feb. 9, 1988, now abandoned.

The present invention is directed to a process for producing alkylene oxides from alkanes and an oxygen-containing gas in the presence of a suitable catalyst under conditions which achieve high efficiency and selectivity toward the desired product.

BACKGROUND OF THE INVENTION

The production of alkylene oxides by oxidation of an appropriate alkene in the presence of a suitable catalyst is well known.

Brian J. Ozero, *Handbook of Chemicals Production Processes*, edited by Robert Meyers, McGraw Hill Book Co. (1986) at Chapter 1.5, discusses cyclic processes using both oxygen and air as oxidant for the production of ethylene oxide (EO) from ethylene. In these processes, the alkene is oxidized in a multitubular catalytic reactor in vapor phase. The reactor off gases are cooled and scrubbed with water in an absorber to recover ethylene oxide which is sent to the recovery section for further purification.

In the oxygen-based process described by Ozero, the scrubber off gases are divided into three parts which are: (i) recycled to the reactor, (ii) vented and (iii) sent to a separator for carbon dioxide removal and recycle of the remaining hydrocarbons. This process suffers from several disadvantages. For example, the oxygen-based ethylene oxide process requires a separate carbon dioxide removal unit and a purge to remove argon to prevent its accumulation.

In the air-based process described by Ozero, the scrubber off gases are sent to a second reactor, which is the purge reactor, where additional unreacted ethylene is reacted using a higher air to ethylene ratio, foregoing some EO selectivity. The reactor off gases are again passed through another water scrubber to recover EO produced. It is known that the volume of hydrocarbons purged, when utilizing air as a source of oxygen, requires that the purge scrubber off gases be incinerated to remove any remaining hydrocarbons in order to meet environmental regulations. In this air-based process, an additional purge oxidation reactor, a water scrubber, and an effluent incinerator are required, as well as a greater volume of catalyst. Also, both this and the oxygen-based process use the expensive ethylene as the raw material. The processes described by Ozero are limited to either pure oxygen or air.

Khoobiar et al., U.S. Pat. No. 4,609,502, discloses a cyclic process for producing acrylonitrile using propane as a starting material. This process differs from the production of oxides by the presence of ammonia and the choice of catalyst. In the process disclosed by Khoobiar et al., the alkane is initially dehydrogenated catalytically in the presence of steam to form propylene. This is in contrast to most conventional dehydrogenation processes which avoid steam primarily due to the costs involved. After ammoxidation, the effluent is quenched to remove the desired product, and the off-gases, including propylene and propane, are sent to an oxidation reactor to remove oxygen by selective reaction with hydrogen to form water vapor. The gas mixture exiting the selective oxidation reactor includes substantial amounts of methane, ethane and ethylene, which are byproducts of dehydrogenation, and unreacted propylene and propane, in addition to carbon oxides. A sufficient portion of this gas mixture is purged to remove the net production of carbon oxides and light hydrocarbons.

Optionally, this gas mixture is split and a portion sent to a separator which removes only carbon dioxide. A portion of the effluent from the separator is purged to remove light hydrocarbons. The nonpurged portion is mixed with the remainder of the oxidation reactor effluent, fresh propane, and steam, if necessary. This mixture is sent to the dehydrogenator where the propane is converted to propylene. Another option is to cool and liquify the $C_3$ hydrocarbons from the oxidation reactor, and then vaporize the hydrocarbons prior to recycle.

In the process disclosed by Khoobiar et al., there is no practical way to remove byproducts of propane dehydrogenation, such as methane, ethane, ethylene and the like, thereby preventing their accumulation in the system, other than by removing them in a purge stream. The removal of these gases in a purge stream will likewise result in a loss of the circulating propane and propylene, thus causing a significant decrease in the overall yield of propylene to acrylonitrile. While, as mentioned above, proPane and propylene can be recovered from the stream prior to venting, this requires additional refrigeration apparatus to cool and liquify the propylene and propane. The separated $C_3$ hydrocarbons must be vaporized prior to recycle. These operations add to the capital and power requirements of the process.

Another disadvantage of the Khoobiar et al. process stems from the use of the selective oxidation reactor to treat the gaseous effluent exiting the quench tower. This quench effluent is at ambient temperature and must be heated prior to introduction into the oxidation reactor in order to promote oxygen removal. Because there is a significant amount of oxygen in the quench effluent, the heat of reaction generated in the oxidation reactor can result in excessive temperatures in the system. There are three know methods to alleviate this problem. First, the amount of oxygen entering the oxidation reactor can be reduced by other means. Second, multiple reactors can be utilized with a cooling means between each pair of reactors. Third, a portion of the oxidation reactor can be passed through a cooling means and recycled to the feed to reduce the internal temperature of the reactor. None of these measures is attractive from the viewpoint of cost and efficiency.

The oxidation reactor in the Khoobiar et al. process is operated with oxidation catalysts such as noble metals (e.g., platinum). Olefins and carbon monoxide, which are generated in the dehydrogenation reactor, are known to deactivate these catalysts, as disclosed in, Charles L. Thomas, *Catalytic Processes and Proven Catalysts*, Academic Press (1970) at 118–119. Accordingly, multiple oxidation reactors must be used (see Khoobiar et al. at column 4, lines 51–56) to allow for frequent regeneration of the catalyst which represents yet another addition to production costs. These consideration apply as well to the catalytic production of oxides from alkanes as contemplated herein.

It is therefore apparent that the industry is still searching for a cost effective process of converting alkanes into oxides. The process of the present invention is cost effective and substantially reduces or eliminates disadvantages of the aforementioned systems. Moreover, in comparison to conventional processes, the thermal requirements of the present invention process are markedly reduced.

SUMMARY OF THE INVENTION

A process is disclosed for the production of oxides comprising converting a gaseous alkane to the corresponding alkene in a multistage dehydrogenator comprising at least three discrete reactors. The product stream containing the alkene and unreacted alkane is withdrawn from a reactor intermediate the first and last reactors. The feed stream is passed through heating means to raise the temperature thereof before each of the discrete reactors up to and including the reactor from which the product stream is withdrawn. The catalyst in the dehydrogenerator is passed through all reactors, regenerated and recycled to the first reactor. The alkene is reacted in an oxidation reactor with an oxygen-containing gas, preferably oxygen-enriched air, in the presence of an oxidation catalyst to form the desired product. The product stream is quenched with a liquid to form a liquid phase containing the desired product and a gas phase which is passed under pressure into a separator, such as a pressure swing adsorption unit, to remove carbon oxides, oxygen, nitrogen when present, and lower hydrocarbons therefrom. The product stream from the separator is recycled into the reactor of the multistage dehydrogenator immediately following that from which the product stream is withdrawn and passed through that reactor and any subsequent reactors. The effluent from the last reactor may be introduced to the first reactor, to an intermediate reactor, or directly to the oxidation reactor. A hydrogen recovery means may be utilized to remove hydrogen from the dehydrogenator product stream for recycle.

DESCRIPTION OF THE PREFERRED EMBODIMENTS

The process of this invention is applicable to the synthesis of oxides. In each instance, an alkene, which has been formed by the dehydrogenation of the corresponding alkane, is reacted with an oxygen-containing gas comprising pure oxygen, air, or a gas enriched in oxygen relative to air, in the presence of a suitable catalyst. The term "suitable oxidation catalyst" indicates a catalyst that will catalyze the production of the desired product, e.g. ethylene oxide from ethylene or propylene oxide from propylene, under the conditions utilized in the reactor. That is, an oxirane ring or alkylene oxide will be formed. In the interest of brevity, the subject process will be described with reference to the production of propylene oxide from propane, but is in no way intended to be limited thereto.

Figure 1:
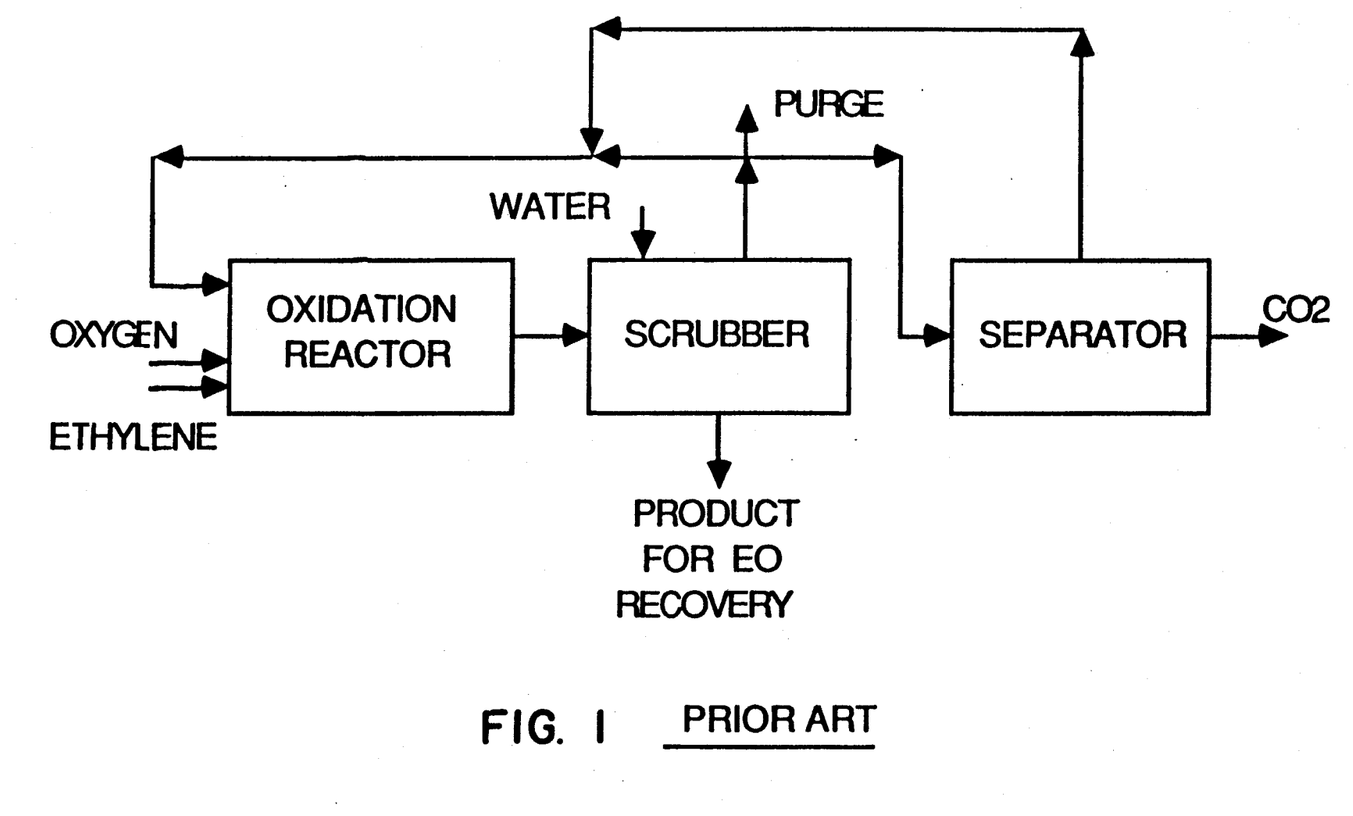
FIG. 1 illustrates in block diagram a conventional process for production of ethylene oxide from ethylene using oxygen.
Figure 2:
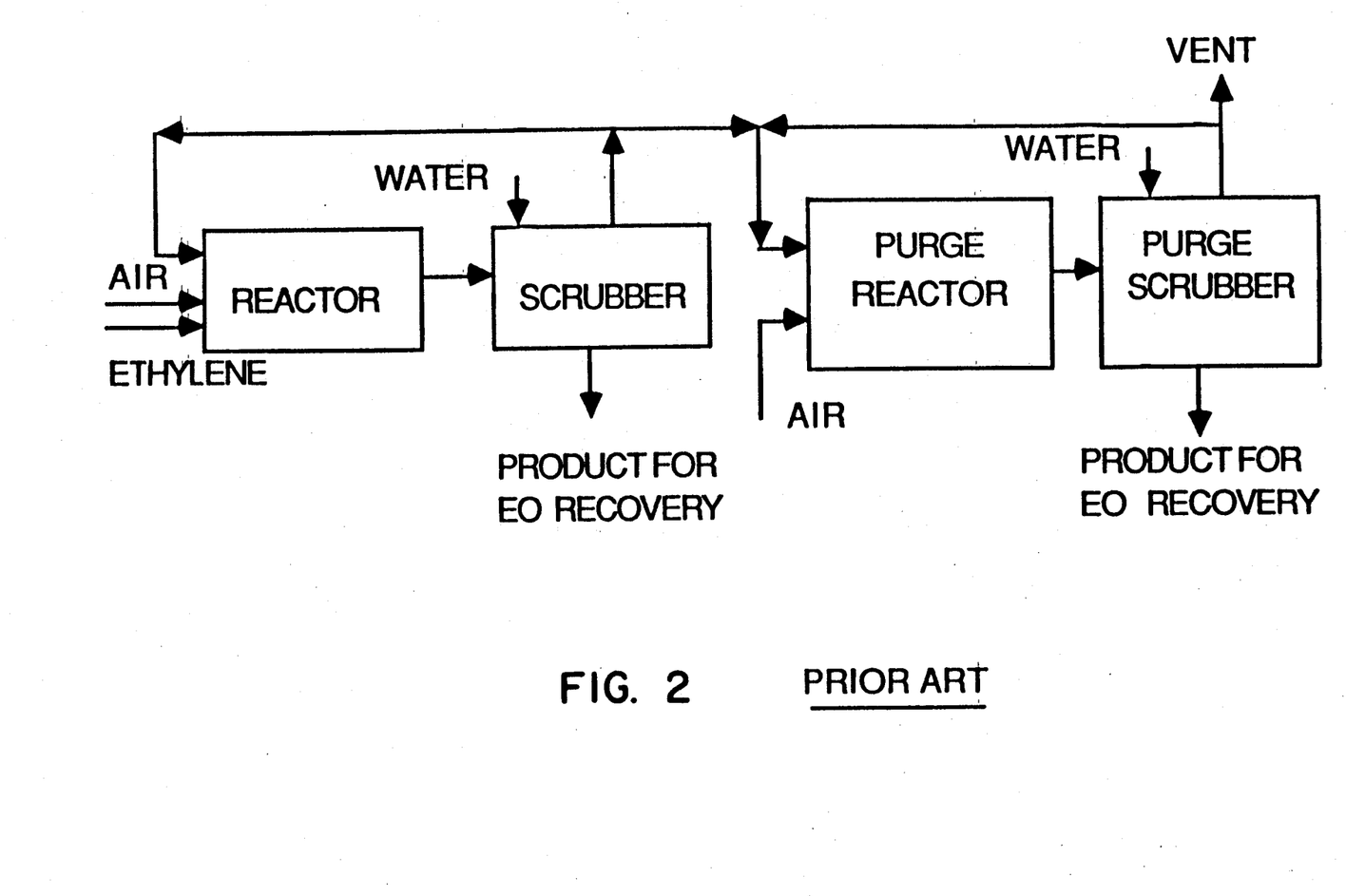
FIG. 2 illustrates in block diagram a conventional process for production of ethylene oxide from ethylene using air.

Turning to the drawings, a process currently utilized commercially to produce oxides such as ethylene oxide, is illustrated in FIGS. 1 and 2. In FIG. 1, ethylene and oxygen are fed into a conventional reactor containing a suitable oxidation catalyst; in FIG. 2, ethylene and air are similarly fed. The reactor may be of any conventional fixed or fluidized bed design. Such processes may employ a recycle step to increase the overall process efficiency. The oxygen concentration in the feed to the reactor is adjusted to maximize the selectivity to the desired product.

In the oxygen-based process, shown in FIG. 1, methane is added continuously to the reactor as a flame suppressor to compensate for the loss in the purge. The reactor off gases are sent to water scrubber to remove products for ethylene oxide recovery. The scrubber off gases are divided into three parts: a first part is recycled back to the reactor, a second part is vented, and a third part is sent to a $CO_2$ removal unit. After removing $CO_2$, the off gases of the third part are sent back to the reactor. The purge is essential to prevent any argon build up in the system. Since there is no other way to remove inerts from the system, one cannot use air or oxygen-enriched air as the oxidant feed since the large volume required to purge the nitrogen would cause excessive loss of product.

In the air-based process, shown in FIG. 2, ethylene and air are fed into the reactor. The reactor products are water scrubbed to remove the ethylene oxide produced. A part of the scrubber off gases are recycled back to the reactor while the remainder is sent to a second reactor. Additional air is added to this second reactor to achieve an air-to-ethylene feed ratio higher than the first reactor so that high ethylene conversion is obtained. The off gases of the second reactor are sent to a second water scrubber to remove and recover the additional ethylene oxide produced. The second scrubber off gases are split into two portions—one is recycled back to the second reactor while the other is purged, typically via incineration.

Figure 3:
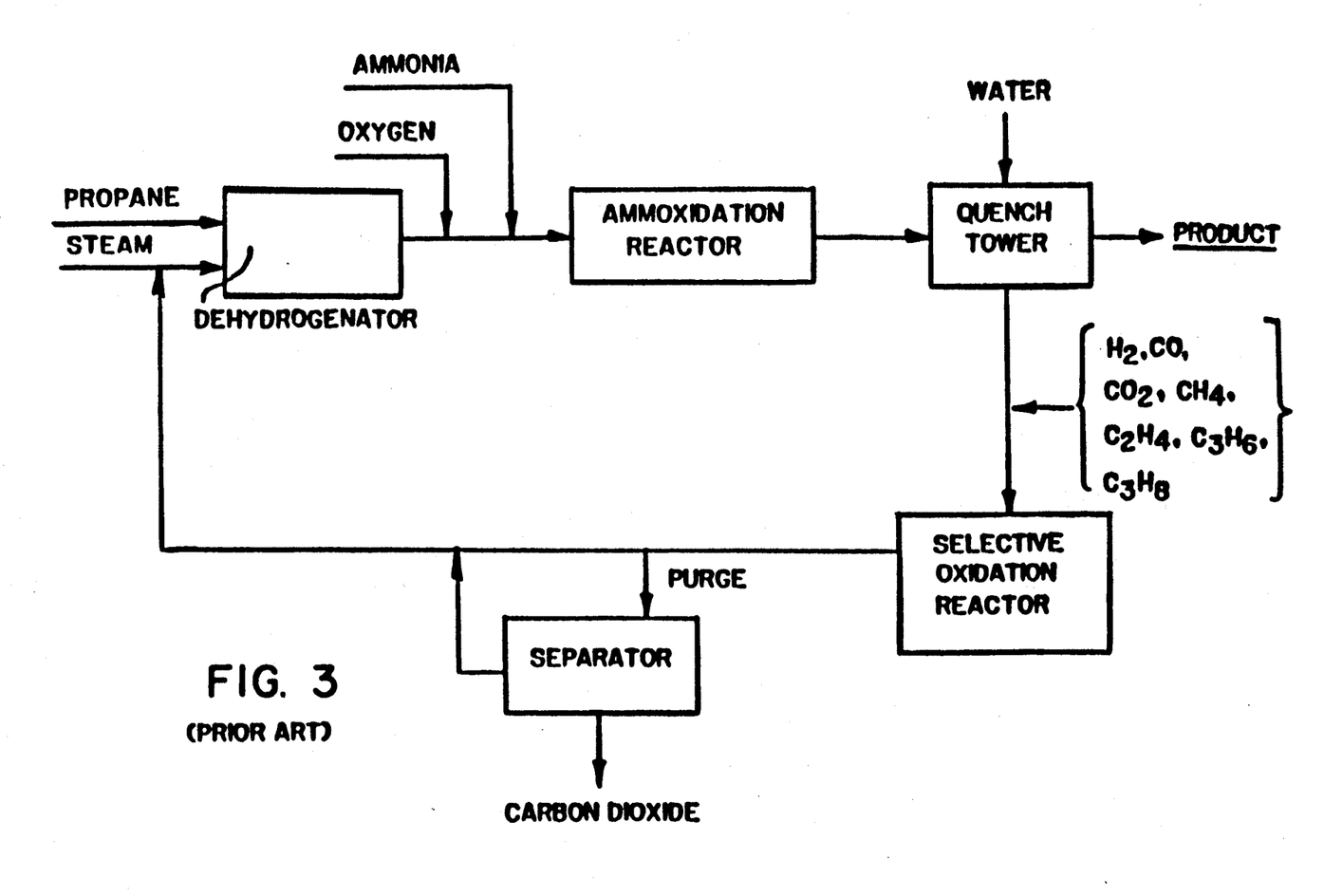
FIG. 3 illustrates in block diagram a conventional process for production of acrylonitrile utilizing a recycle step.

FIG. 3 illustrates the cyclic process for producing acrylonitrile as disclosed in Khoobiar et al., U.S. Pat. No. 4,609,502. In this process, propane and steam are fed into a dehydrogenator to form propylene, which is then mixed with oxygen and ammonia and fed into an ammoxidation reactor. The product of the reactor is fed to an aqueous quench tower, and the products withdrawn in solution. The gaseous off gases from the quench tower, typically containing hydrogen, carbon monoxide, carbon dioxide, methane, ethylene, ethane, propane, propylene, and oxygen is fed to a selective oxidation reactor. It is generally essential for the efficient operation of such a reactor to heat the gas mixture prior to introduction therein.

A portion of the off gas from the selective oxidation reactor is passed to a separator to remove carbon dioxide by an undisclosed mechanism. A portion of the selective oxidation reactor effluent, which contains light hydrocarbons and hydrogen, is purged, treated to remove propane and propylene [not shown], and then discarded, thereby preventing buildup of byproducts in the system. The propane and propylene removed are combined [not shown] with the remainder of the selective oxidator effluent and the remainder of the separator effluent and recycled to the dehydrogenator. It is, of course, necessary for the selective oxidation reactor to be effective in removing all oxygen from the quench tower effluent to prevent significant loss of effectiveness of the dehydrogenator. It is also necessary for the oxygen feed to be pure oxygen since the use of air or oxygen-enriched air would produce a rapid accumulation of nitrogen in the system. This would, in turn, require the purging of a larger portion of the recycle stream with resulting loss of efficiency.

Figure 4:
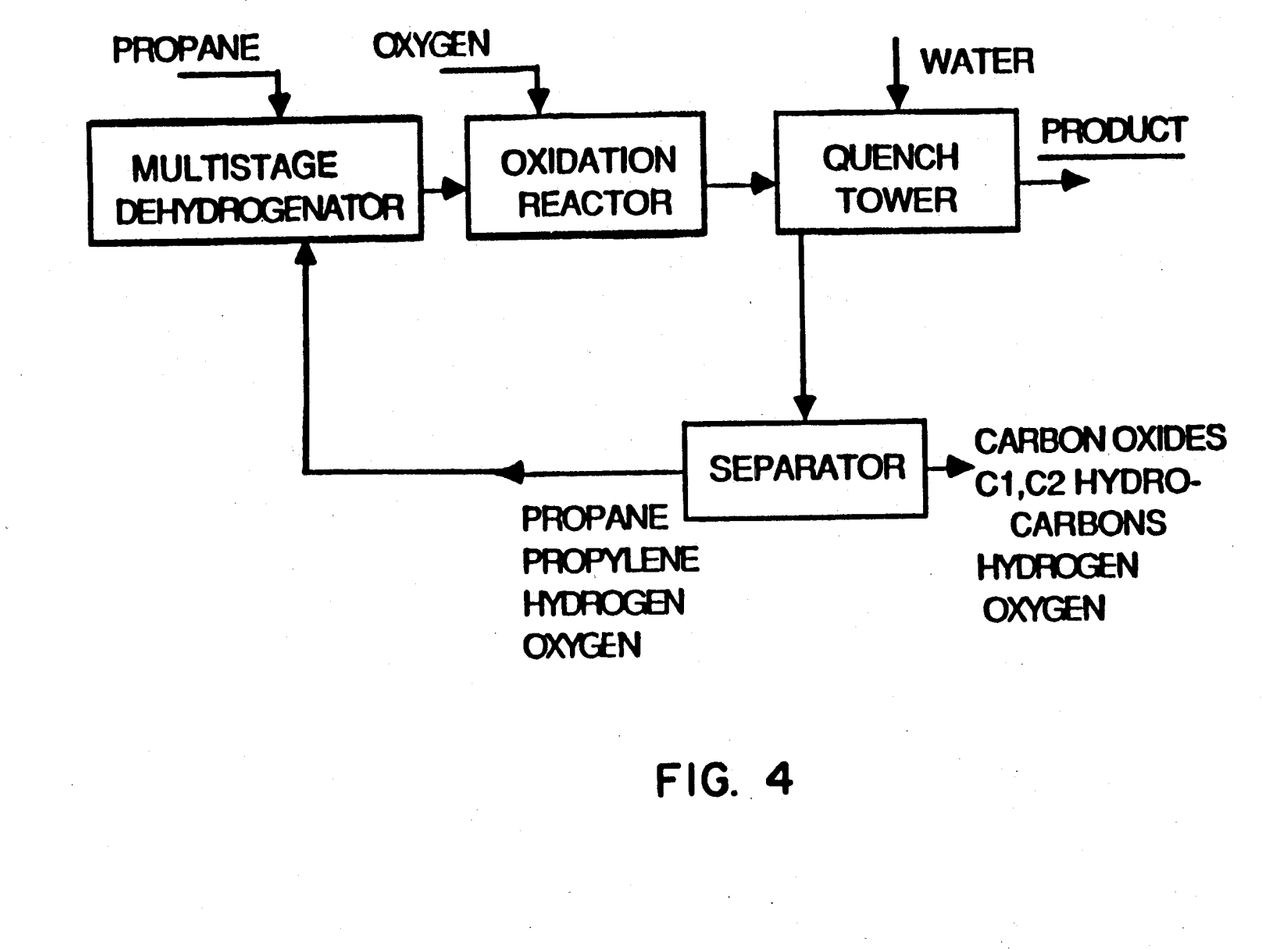
FIG. 4 illustrates in block diagram the process of the present invention for production of propylene oxide.

The process of the present invention is illustrated in FIG. 4. The present process provides the efficiency of recycle afforded by the process illustrated in FIG. 3, yet does not require the capital cost of selective oxidation units, does not have a loss of efficiency through a purge stream, and does not lose effectiveness of the dehydrogenation catalyst due to oxygen in the recycle stream thereto. In addition, unexpectedly, the process of the present invention can advantageously and efficiently utilize air and oxygen-enriched air as a feed to the oxidation reactor.

Referring to FIG. 4, propane is fed into the multi-stage dehydrogenator where it is converted to propylene. For increased catalyst life, it is preferred to introduce a hydrogen-containing gas into the dehydrogenator with the propane feed. The dehydrogenator will be discussed in detail below. The catalyst utilized in the dehydrogenator can be any conventional dehydrogenation catalyst, preferably one or more Group VIII noble metals such as platinum on an alumina support. The effluent product stream from the dehydrogenator comprising unreacted propane, propylene and hydrogen, is fed into a conventional oxidation reactor along with pure oxygen, air or, preferably, oxygen-enriched air.

The oxidation reactor utilized in the present process is conventional and may employ either a fixed, fluidized or slurry bed reactor design and appropriate catalyst. The reaction may be carried out either in gas or liquid phase. If it is carried out in a liquid phase, a suitable solvent may also be employed. The reactor contains a suitable oxidation catalyst such as silver oxide, molybdenum oxide, rhethenium oxide, or lanthanum oxide, alone or in combination with others, and they may be supported or unsupported. Various catalysts are disclosed, for example, in Fenton. U.S. Pat. No. 3,316,279, Waddan et al., European Patent Appln. No. 0 043 192, Bryce Smith, Great Britain Patent 1,409,421, Bobolev, Great Britain Patent Nos. 1,433,885, and 1,433,886, Kolombos et al., U.S. Pat. Nos. 3,888,889. Additional suitable catalysts are known to those skilled in the art.

The oxidation reaction is conducted at a temperature of from about 100° to 500° C., preferably from about 150° to 350° C., at a pressure typically in the range of from about zero (0) to 1000 psig, preferably from about 15 to 750 psig. The reactor residence times vary depending upon the catalyst, as is well know to those skilled in the art, from a few seconds up to 1 hour. The oxygen-containing gas feed may be pure oxygen, air or oxygen-enriched air. In accordance with this invention, oxygen-enriched air preferably contains from about 30 to 80, most preferably from about 55 to 65, percent by volume of oxygen. Such mixtures may be produced by adjusting the capacity of a conventional oxygen-producing unit, e.g. a conventional pressure swing adsorption unit, or by mixing pure oxygen with air in the proper proportions. The ratio of oxygen to propylene in the feed converted to products is suitably in the range of from about 0.8:1 to 2.0:1 by volume.

The effluent from the oxidation reactor comprises a major amount of propylene oxide and minor amounts of acetone, acetaldehyde, formaldehyde, carbon oxides, and nitrogen, when present in the feed, as well as unreacted oxygen, propylene and propane. This gaseous mixture is quenched or scrubbed with a liquid, such as water, to dissolve the water-soluble compounds for subsequent separation and recovery of propylene oxide.

The gas phase effluent from the quench step is introduced into a separator, e.g., a membrane unit, an absorber, a pressure swing adsorption (PSA) unit or a cryogenic system. These separators can be used alone or in combination depending on whether pure oxygen or enriched air is utilized as the feed as is well known to those skilled in the art. For example, if enriched air is used as the feed, a membrane followed or preceded by a PSA unit can be used to prevent any nitrogen accumulation. For purpose of illustration, a PSA unit will be used.

PSA is a well known process for separating the components of a mixture of gases by virtue of the difference in the degree of adsorption among them on a particular adsorbent retained in a stationary bed. Typically, two or more such beds are operated in a cyclic process comprising adsorption under relatively high pressure and desorption or bed regeneration under low pressure or vacuum. The desired component or components may be obtained during either of these stages. The cycle may contain other steps in addition to the fundamental steps of adsorption and regeneration, and it is commonplace to have two or more adsorbent beds cycled out of phase to assure a pseudocontinuous flow of desired product. It is preferred to pass the quench tower effluent through a conventional dryer (not shown) to remove moisture therefrom prior to introducing it into the PSA unit.

It may be necessary to raise the pressure of the quench tower effluent in a compressor or other suitable means prior to introducing it into the PSA unit. The compressor increases the pressure of the quench tower gaseous effluent to the operating pressure of a PSA unit, which typically functions from about 3 to 50 psi, preferably from about 20 to 40 psi, higher than the quench tower. These ranges may vary to an extent depending on the adsorbent in the PSA unit.

The adsorbent in the PSA unit may be any art-recognized material which will adsorb propane and propylene to a substantially greater degree than carbon oxides, nitrogen and oxygen, or vice versa. Silica gel or a conventional molecular sieve material, such as 4A zeolite, are preferred adsorbent materials. Silica gel is a particularly preferred material where oxygen-enriched air is utilized as a reactor feed material.

The PSA unit produces a recycle stream and a waste stream. The latter is comprised of oxygen, carbon oxides, e.g. carbon monoxide and carbon dioxide, nitrogen, where the oxidation reactor feed is air or oxygen-enriched air, and $C_{1-2}$ hydrocarbons, e.g. methane, ethane and ethylene, as well as trace amounts of propane and propylene. The PSA recycle stream contains propane, propylene, and a minor quantity of oxygen, typically less than about 2 percent by volume of oxygen.

The oxygen content in the recycle stream would ordinarily have an adverse effect on the efficiency of the dehydrogenator. This is readily apparent, for example, from Khoobiar et al. wherein it is required that the effluent from the quench tower be fed into a selective oxidation reactor.

The use in the PSA unit of an adsorbent, such as a silica gel, which will adsorb propane and propylene will cause substantially all of the hydrogen in the quench tower effluent to be withdrawn and removed in the waste stream. Therefore, it is necessary to add an appropriate quantity of hydrogen to the propane/propylene recycle stream before introducing it into the dehydrogenator. Where an adsorbent which adsorbs carbon dioxide, such as 4A zeolite molecular sieve, is used as the adsorbent in the PSA unit, the hydrogen will be withdrawn in the recycle stream. Therefore, it will not be necessary to add hydrogen thereto. In fact, it will typically be necessary to remove some hydrogen therefrom to prevent excessive build-up in the system.

In a preferred embodiment of the present invention, a PSA system comprising parallel PSA units each containing one of the two types of adsorbers mentioned above is utilized wherein the feed is disproportionately divided between them so that the combined effluents contain the desired amount of hydrogen. The waste streams are discarded. The amount of hydrogen required in the recycle feed to the dehydrogenator will vary with the catalyst and can be determined by one skilled in the art.

Figure 5:
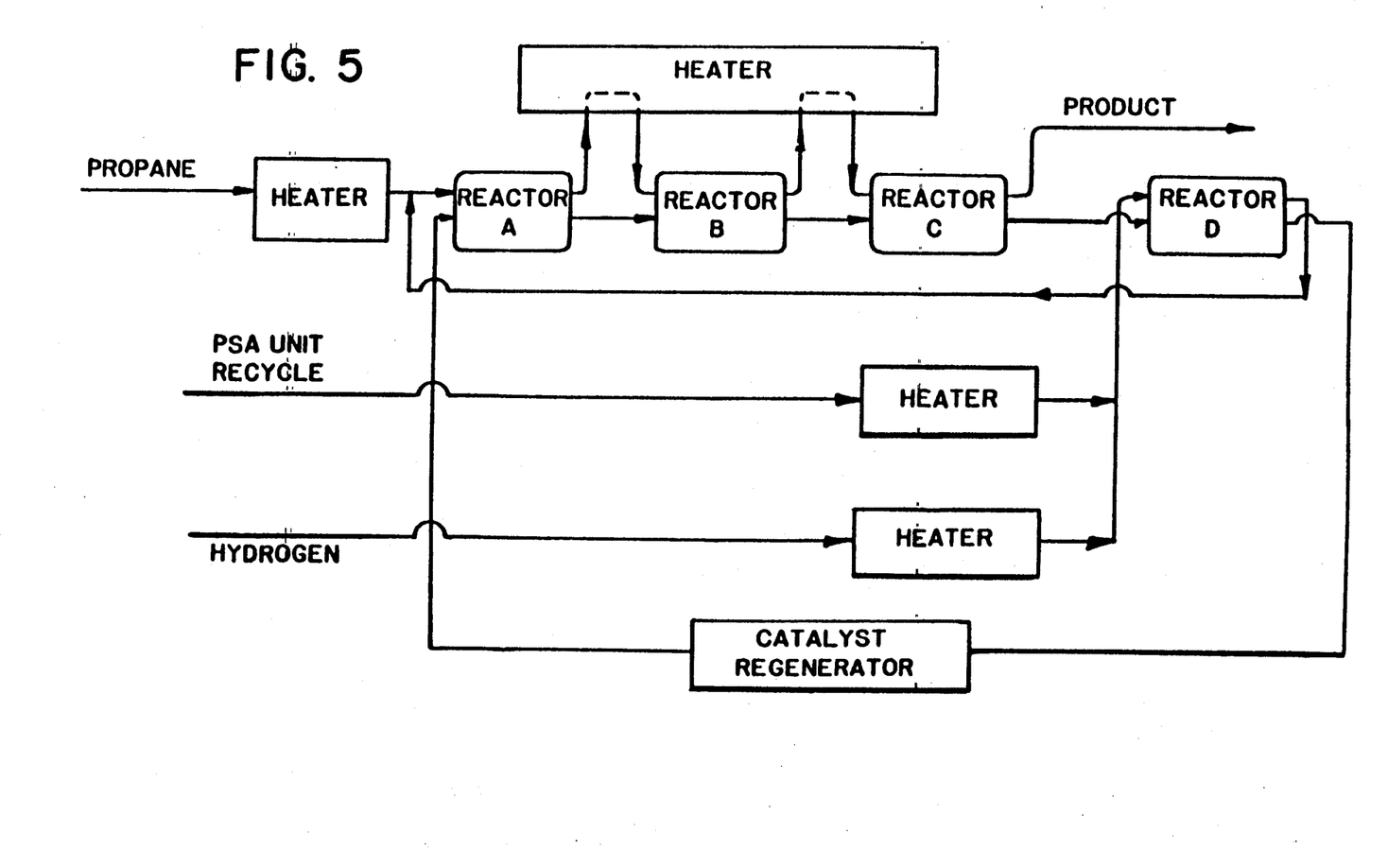
FIG. 5 illustrates in block diagram the dehydrogenator utilized in the process the present of this invention.

As shown in FIG. 5, the present invention utilizes a multistage dehydrogenator which is efficient and which, modified in accordance with the present invention, eliminates the need for the selective oxidation reactor in Khoobiar et al. The use of a multistage catalytic reactor is described in the literature, e.g. Pujado et al., *Catalytic Conversation of LPG*, American Institute of Chemical Engineers (April 6–10, 1986). In such reactors, the catalyst sequentially flows through a series of discrete reactors and is withdrawn at the end for regeneration and recycle. The reactant gas stream likewise flows through the reactors and is withdrawn into a heating means between each of the individual reactors. The dehydrogenator typically operates at a temperature of from about 500° to 800° C., preferably from about 550° to 700° C. The reheating of the reactant stream as it flows through the reactors is especially beneficial for an endothermic reaction such as the conversion of propane to propylene.

In accordance with the present invention, the reactant gas stream does not flow through all reactors, but is withdrawn as a product stream from a reactor intermediate the first and last reactors. Preferably, there are at least four reactors and the product stream is withdrawn from the penultimate reactor. It is beneficial to withdraw the product stream from a latter stage of the dehydrogenator to obtain maximum efficiency therefrom. The reheating of the reactant stream takes place only up to and including the reactor from which the product stream is withdrawn.

If the PSA recycle was passed to the first reactor along with fresh propane, then selectivity to propylene of the first reactor will be low due to the presence of minor quantities of oxygen. Therefore, the recycle stream from the PSA unit, comprising unreacted alkane and alkene, and minor amounts of oxygen and nitrogen, if present, is introduced into the reactor following that from which the product is withdrawn, and passed therethrough and through subsequent reactors, if any, thereby substantially eliminating low oxygen content thereof without detriment to the system. The PSA recycle gas is passed through a dehydrogenation reactor to which there is no fresh propane addition in order to remove any oxygen remaining; then the resulting gas stream and fresh propane are passed to the first dehydrogenation reactor for reaction.

As is evident from FIG. 5, the initial propane feed passes through reactors A through C and is thereafter withdrawn for passage to the oxidation reactor, see FIG. 4. The recycle stream from the PSA unit is heated, introduced into reactor D and thereafter introduced into the process as described above. The spent catalyst withdrawn from reactor D is passed through a conventional catalyst regenerator and returned to reactor A. In the regenerator, accumulated carbon is burned off of the catalyst after which it is chemically reduced.

In the embodiment illustrated in FIG. 5, the effluent from the final reactor of the dehydrogenator is introduced into the initial feed stream. In the event that the alkene concentration in the feed to one of the intermediate reactors more closely approximates the concentration of the effluent from the final reactor than does the concentration of the initial feed, then the final reactor effluent is preferably introduced into such intermediate reactor. It is further contemplated herein to introduce the effluent from the final reactor directly to the oxidation reactor if the propylene content thereof is sufficiently high. This might occur, for example, when the PSA effluent passes through two or more reactors of the dehydrogenator.

In the event that the recycle stream from the PSA unit contains no hydrogen, it is combined with a hydrogen-containing stream at elevated temperature prior to entry into the dehydrogenation reactor, in which hydrogen reacts with any oxygen contained in the recycle stream. The resulting oxygen-free effluent is introduced into the initial feed, an intermediate reactor, or the oxidation reactor. In the event that the effluent is not introduced into the initial feed, one may add hydrogen to the initial feed to prolong the life of the catalyst.

It will be appreciated by those skilled in the art that a single heater can be utilized in FIG. 5 with all streams flowing therethrough. Further, the hydrogen-containing stream in FIG. 5 can be a stream of medium purity hydrogen obtained from an external source, or a recycle hydrogen stream from within the process. The hydrogen added to the initial feed can likewise be recycled or obtained from an external source. Hydrogen may also be supplied to the heater in combination with an oxygen feed for combustion. Hydrogen recycle can be obtained from the stream, also containing propane and propylene, produced by the PSA unit when the adsorbent therein adsorbs carbon dioxide as described above. Hydrogen recyle can also be obtained in the same manner from the product stream of the dehydrogenator before it is introduced into the oxidation reactor. It is preferred, as stated previously, to utilize a PSA system containing parallel PSA units each containing a different adsorbent and combining their effluents into a recycle stream containing the proper amount of hydrogen.

For the system as shown in FIG. 4, total flow in moles and compositions in mole percent at various points in the system are presented in Table I based on 100 mole of propylene oxide produced. The propane feed was virtually 100 percent propane, and the feed to the oxidation reactor was pure oxygen. For the examples shown in Tables I and II, silica gel is the adsorbent. Propylene conversion is defined as moles of propylene converted to products to moles of propylene fed to the oxidation reactor. For example in Table I:

$$\text{conversion} = 100 \times \frac{1461.9 \times .489 - 1418.3 \times .403}{1461.9 \times .489}$$
$$= 20.1\%$$

In Table I, Point A is the feed into the dehydrogenator after the stream from the final stage thereof has been combined with fresh propane, Point B is the combined feed into the oxidation reactor, Point C is the oxidation reactor effluent, Point D is the quench tower gaseous effluent, Point E is the recycle stream from the PSA unit and Point F is the PSA unit waste stream.

TABLE I

Propane to Propylene Oxide (PO) Process — Pure $O_2$ Feed + Propylene Conversion = 20%

| Component | A % | B % | C % | D % | E % | F % |
|---|---|---|---|---|---|---|
| $C_3H_6$ | 50.0 | 48.9 | 40.3 | 47.1 | 61.3 | 8.7 |
| $C_3H_8$ | 43.8 | 19.5 | 20.1 | 23.6 | 30.7 | 4.4 |
| $O_2$ | — | 13.6 | 2.0 | 5.9 | 0.4 | 20.6 |
| PO | — | — | 7.1 | — | — | — |
| Acetone | — | — | 0.6 | — | — | — |
| ACOH | — | — | 0.5 | — | — | — |
| HCHO | — | — | 0.3 | — | — | — |
| $CH_3CHO$ | — | — | 0.3 | — | — | — |
| CO | — | — | 0.6 | 0.7 | 0.1 | 2.5 |
| $CO_2$ | 4.7 | 3.5 | 8.2 | 5.3 | 5.8 | 3.9 |
| $H_2$ | — | — | 5.1 | — | — | — |
| $CH_4$ | 0.7 | 2.4 | 2.5 | 3.0 | 0.8 | 8.7 |
| $C_2H_4$ | 0.1 | 0.5 | 0.5 | 0.6 | 0.2 | 1.8 |
| $C_2H_6$ | 0.2 | 0.7 | 0.8 | 0.9 | 0.2 | 2.6 |
| $H_2$ | 0.4 | 10.8 | 11.2 | 13.0 | 0.5 | 46.8 |
| Flow, moles | 1086.4 | 1461.9 | 1418.3 | 1212.6 | 885.1 | 327.4 |

Again utilizing a system as shown in FIG. 4 for the production of propylene oxide with propane as a starting material, the oxygen feed to the oxidation reactor was changed to a mixture of equal parts of pure oxygen and air which produced oxygen-enriched air containing approximately 60 percent of oxygen. The flow at the same points in the system were determined and are presented in Table II. The data expressed in Table II, as in Table I, represents operation of the system under conditions such that 20 percent of the propylene in the oxidation reactor is converted therein to different products, including propylene oxide.

TABLE II

Propane to Propylene Oxide (PO) Process — 50% $O_2$ + 50% Air Feed
Propylene Conversion = 20%

| Component | A % | B % | C % | D % | E % | F % |
|---|---|---|---|---|---|---|
| $C_3H_6$ | 50.0 | 44.7 | 36.8 | 42.3 | 61.0 | 6.2 |
| $C_3H_8$ | 43.8 | 17.9 | 18.4 | 21.1 | 30.5 | 3.1 |
| $O_2$ | — | 12.6 | 2.0 | 5.8 | 0.4 | 16.0 |
| PO | — | — | 6.4 | — | — | — |
| Acetone | — | — | 0.6 | — | — | — |
| ACOH | — | — | 0.4 | — | — | — |
| HCHO | — | — | 0.3 | — | — | — |
| $CH_3CHO$ | — | — | 0.3 | — | — | — |
| CO | — | — | 0.6 | 0.6 | 0.1 | 1.8 |
| $CO_2$ | 4.7 | 3.2 | 7.5 | 4.8 | 5.8 | 2.8 |
| $H_2O$ | — | — | 4.7 | — | — | — |
| $CH_4$ | 0.7 | 2.2 | 2.3 | 2.6 | 0.8 | 6.2 |
| $C_2H_4$ | 0.1 | 0.5 | 0.5 | 0.5 | 0.2 | 1.2 |
| $C_2H_6$ | 0.2 | 0.7 | 0.7 | 0.8 | 0.2 | 1.9 |
| $H_2$ | 0.4 | 9.9 | 10.2 | 11.7 | 0.5 | 33.2 |
| $N_2$ | — | 8.3 | 8.5 | 9.8 | 0.5 | 27.8 |
| Flow, moles | 1086.4 | 1597.3 | 1553.7 | 1352.1 | 889.5 | 462.6 |

The process of this invention is advantageous in that it is very efficient and is cost attractive in comparison to prior art processes requiring a selective oxidation unit. In addition, the process of the invention has a comparatively small incidence of build-up of any of the undesirable components of the various gaseous streams formed at any stage thereof. Further, the subject process can be utilized with air or oxygen-enriched air as a feed to the oxidation reactor, heretofore not feasible with a closed loop system. Unexpectedly, the subject process operates at particularly enhanced efficiency with an oxygen-enriched air feed.

The invention has been described with reference to preferred embodiments thereof. It will be appreciated by those skilled in the art that various modifications may be made from the specific details given without departing from the spirit and scope of the invention.

We claims:

1. A process for the production of alkylene oxides comprising:
   (a) forming an alkene from a gaseous alkane by passage through a multistage catalytic dehydrogenator, comprised of a series of at least three discrete catalytic reactors, wherein a dehydrogenator product stream containing said alkene and unreacted alkane is withdrawn from a reactor intermediate the first and last of said reactors, wherein the gaseous flow between all of said reactors in sequence, up to and including the reactor from which the product stream is withdrawn, is passed through a heating means to raise the temperature thereof, and wherein the catalyst in the dehydrogenator is passed through all of said reactors, regenerated and recycled to the first reactor;
   (b) introducing said alkene stream and an oxygen source selected from the group consisting of pure oxygen, air or a gas enriched in oxygen relative to air into suitable oxidation reactor for reaction in the presence of an oxidation catalyst to about 100° to 500° C. 0 to 1000 psig, and a residence time from a few seconds up to 1 hour to produce a gaseous effluent containing said oxide;
   (c) quenching said gaseous effluent in a liquid to form a liquid phase containing said oxide and a gas phase;
   (d) recovering said oxide from the liquid phase;
   (e) introducing the gas phase quench effluent under pressure into a pressure swing adsorption unit to thereby form (i) a waste stream, and (ii) a gaseous stream comprising said unreacted alkane, alkene, a minor amount of oxygen, and nitrogen when air or oxygen-enriched air is introduced as the oxygen source into the reactor in step (b);
   (f) introducing said gaseous stream into the reactor in said dehydrogenator which immediately follows in sequence the intermediate reactor from which the product stream was withdrawn, thereby removing substantially all of the oxygen contained in said stream;
   (g) recycled the effluent from the last reactor of said dehydrogenator to another reactor of said dehydrogenator.

2. A process in accordance with claim 1, wherein another reactor of step (g) is the first reactor of the dehydrogenator.

3. A process in accordance with claim 1, wherein another reactor of step (g) is a reactor of said dehydrogenator other than said first reactor wherein the concentration of alkene in the stream entering another reactor is approximately the same as that of the effluent from the last reactor of said dehydrogenator.

4. A process in accordance with claim 1, wherein another reactor is the intermediate reactor of said dehydrogenator.

5. A process in accordance with claim 1, wherein the dehydrogenator contains at least four reactors and the product stream is withdrawn from the penultimate reactor.

6. A process in accordance with claim 1, wherein the alkane is propane, the alkene is propylene, and the alkylene oxide is propylene oxide.

7. A process in accordance with claim 1, wherein the oxygen source is oxygen-enriched air containing from about 30 to about 80 percent of oxygen by volume and the gaseous stream formed in step (e) additionally contains a minor amount of nitrogen.

8. A process in accordance with claim 7, wherein the oxygen-enriched air contains from about 55 to about 65 percent by volume of oxygen.

9. A process in accordance with claim 1, wherein the gas phase in step (e) is introduced into the pressure swing adsorption unit at a pressure of from about 3 to about 50 psig.

10. A process in accordance with claim 1, wherein oxygen source is oxygen-enriched air, the pressure swing adsorption PSA unit removes substantially all of the hydrogen from the quench effluent, and the PSA effluent is combined with a hydrogen-containing stream prior to introduction into said reactor.

11. A process in accordance with claim 1, wherein the adsorbent in the pressure swing adsorption unit is a silica gel or a molecular sieve.

12. A process in accordance with claim 1, wherein the oxygen source is pure oxygen.

13. A process in accordance with claim 1, wherein the oxygen source is pure oxygen, the gaseous stream formed in step (e) contains substantially all of the hydrogen in the quench effluent, and said gaseous stream effluent is treated to remove excess hydrogen prior to recycle to the dehydrogenator.

14. A process in accordance with claim 13, wherein at least a portion of said removed hydrogen is recycled to the feed of the dehydrogenator.

15. A process in accordance with claim 1, wherein a portion of hydrogen is removed from the dehydrogenator effluent prior to introduction of said effluent into the oxidation reactor in step (b), and said removed hydrogen is recycled to the feed of the dehydrogenator.

16. A process in accordance with claim 1, wherein the oxygen source is air.

17. A process in accordance with claim 1, wherein the temperature in the dehydrogenator is from about 500° to about 800° C.

18. A process in accordance with claim 1, wherein the alkane is ethane, the alkene is ethylene and the oxide is ethylene oxide.

19. A process in accordance with claim 1, wherein the gas phase of step (c), comprising hydrogen, is divided with the resultant divided streams introduced into two pressure swing adsorption units operating in parallel, each unit containing a different adsorbent such that the first gaseous phase formed in the first pressure swing adsorption unit contains a portion of the hydrogen, whereas the second gaseous phase formed in the second pressure swing adsorption unit contains no hydrogen, and wherein the gas phase of step (c) is divided disproportionately between said pressure swing adsorption units so that the gaseous phases formed by said pressure swing adsorption units, when combined, contain a predetermined concentration of hydrogen.

20. A process in accordance with claim 19, wherein the first pressure swing adsorption unit which produces a hydrogen-containing first gaseous phase contains a 4A zeolite molecular sieve adsorbent and the second pressure swing adsorption unit contains a silica gel adsorbent.

21. A process for the production of alkylene oxides comprising:
(a) forming an alkene from a gaseous alkane by passage through a multistage catalytic dehydrogenator, comprised of a series of at least three discrete catalytic reactors, wherein a dehydrogenator product stream containing said alkene and unreacted alkane is withdrawn from a reactor intermediate the first and last of said reactors, wherein the gaseous flow between all of said reactors in sequence, up to and including the reactor from which the product stream is withdrawn, is passed through a heating means to raise the temperature thereof, and wherein the catalyst in the dehydrogenator is passed through all of said reactors, regenerated and recycled to the first reactor;
(b) introducing said alkene stream and an oxygen source selected from the group consisting of pure oxygen, air or a gas enriched in oxygen relative to air into a suitable oxidation reactor for reaction in the presence of an oxidation catalyst at about 100° to 500° C. 0 to 1000 psig, and a residence time from a few seconds up to 1 hour to produce a gaseous effluent containing said oxide;
(c) quenching said gaseous effluent in a liquid to form a liquid phase containing said oxide and a gas phase;
(d) recovering said oxide from the liquid phase;
(e) introducing the gas phase quench effluent under pressure into a separation unit to thereby form (i) a waste stream, and (ii) a gaseous stream comprising said unreacted alkane, alkene, a minor amount of oxygen, and nitrogen when air or oxygen-enriched air is introduced as the oxygen source into the reactor in step (b);
(f) introducing said gaseous stream into the reactor in said dehydrogenator which immediately follows in sequence the intermediate reactor from which the product stream was withdrawn, thereby removing substantially all of the oxygen contained in said stream;
(g) recycling the effluent from the last reactor of said dehydrogenator to another reactor of said dehydrogenator.

22. A process in accordance with claim 21, wherein the separator is chosen from the group consisting of a membrane, an absorber, a pressure swing adsorption unit, a cryogenic system, and combinations thereof.

* * * * *

UNITED STATES PATENT AND TRADEMARK OFFICE
CERTIFICATE OF CORRECTION

PATENT NO. : 5,008,412

DATED : April 16, 1991

INVENTOR(S) : Ramachandran, MacLean and Satchell

It is certified that error appears in the above-identified patent and that said Letters Patent is hereby corrected as shown below:

In the Claims

Col. 10, line 38, after the word "into" insert the word --a--.
        line 39, delete "to" and substitute therefor --at--.
        line 40, after "500° C" delete "." and substitute therefor --,-- (a comma).
        line 60, delete "recycled" and substitute therefor --recycling--.

Col. 12, line 36, after "500° C" delete "." and substitute therefor --,-- (a comma).

Signed and Sealed this

Fifth Day of October, 1993

Attest:

BRUCE LEHMAN

*Attesting Officer*  *Commissioner of Patents and Trademarks*